(12) United States Patent
Aguirre, Jr.

(10) Patent No.: US 11,420,095 B2
(45) Date of Patent: Aug. 23, 2022

(54) BREATH CONTROL DEVICE

(71) Applicants: Milton E Aguirre, Jr., The Hague (NL); MILTON MEDICAL, The Hague (NL)

(72) Inventor: Milton E Aguirre, Jr., The Hague (NL)

(73) Assignee: Livotion LLC, Amherst, MA (US)

( * ) Notice: Subject to any disclaimer, the term of this patent is extended or adjusted under 35 U.S.C. 154(b) by 161 days.

(21) Appl. No.: 16/648,455

(22) PCT Filed: Sep. 12, 2018

(86) PCT No.: PCT/IB2018/001146
§ 371 (c)(1),
(2) Date: Mar. 18, 2020

(87) PCT Pub. No.: WO2019/058174
PCT Pub. Date: Mar. 28, 2019

(65) Prior Publication Data
US 2020/0269087 A1    Aug. 27, 2020

(30) Foreign Application Priority Data
Sep. 19, 2017 (NL) ..................... 2019578

(51) Int. Cl.
*A63B 23/18* (2006.01)
*A63H 33/00* (2006.01)

(52) U.S. Cl.
CPC ............. *A63B 23/18* (2013.01); *A63H 33/00* (2013.01)

(58) Field of Classification Search
CPC ... A63B 23/18; A63B 23/16; A63B 21/00189; A63B 21/023; A63B 21/045; A63B 21/00076; A63B 21/00185; A63B 21/0087; A63B 21/026; A63B 2071/0655; A63H 33/00; A61M 21/02; A61M 2021/0005; A61M 2021/0022; A61M 15/00; G10K 5/00
See application file for complete search history.

(56) References Cited

U.S. PATENT DOCUMENTS 917,271 A    4/1909  Elliott et al.
1,392,700 A  * 10/1921 Oyen ..................... A63B 23/18
                                                 482/13

(Continued)

OTHER PUBLICATIONS

International Searching Authority; International Search Report and Written Opinion of the International Searching Authority; International Application No. PCT/IB2018/001146; Patent Cooperation Treaty; pp. 1-5; publisher European Patent Office; Published Rijswijk, Netherlands; dated Jan. 22, 2019; copy enclosed (5 pages).

(Continued)

*Primary Examiner* — Andrew S Lo
(74) *Attorney, Agent, or Firm* — Metz Lewis Brodman Must O'Keefe LLC (57) ABSTRACT

A breath control device comprising t least one longitudinal tube with a wall with at least a resilient part, wherein the tube is embodied with a proximal open end and a closed distal end, and that the wall of the tube is provided with one or more at least in part active user-controlled closable openings or slits so that the fidgeting device also embodies a breath exercise device.

4 Claims, 8 Drawing Sheets

(56) References Cited

U.S. PATENT DOCUMENTS

| | | | |
|---|---|---|---|
| 1,626,198 A | 4/1927 | Jacquemin | |
| 2,292,474 A | 8/1942 | Paxton | |
| 2,478,323 A | 4/1946 | Rohner | |
| 2,778,263 A | 1/1957 | Ruben | |
| 3,588,041 A * | 6/1971 | Johannisson | A61M 15/0018 251/285 |
| 4,054,134 A * | 10/1977 | Kritzer | A63B 21/00069 482/13 |
| 4,221,381 A * | 9/1980 | Ericson | A63B 23/18 73/239 |
| 4,739,987 A * | 4/1988 | Nicholson | A63B 23/18 482/13 |
| 4,770,413 A * | 9/1988 | Green | A63B 23/18 482/13 |
| 4,798,313 A | 1/1989 | Farley | |
| 4,854,574 A * | 8/1989 | Larson | A63B 23/18 482/13 |
| 4,944,306 A | 7/1990 | Alvino | |
| 6,726,598 B1 * | 4/2004 | Jarvis | A63B 23/18 482/13 |
| 6,986,745 B2 * | 1/2006 | Farr | A61B 5/087 600/533 |
| 8,118,713 B2 * | 2/2012 | Foley | A63B 21/00069 482/13 |
| 8,177,689 B2 * | 5/2012 | Rutten | A63B 21/00069 482/13 |
| 8,327,849 B2 * | 12/2012 | Foley | A61M 16/208 482/13 |
| 8,459,255 B2 | 6/2013 | Spurling et al. | |
| 10,086,166 B1 * | 10/2018 | Nashed | A61M 16/0891 |
| 11,247,098 B2 * | 2/2022 | Gwon | A63B 23/18 |
| 2006/0178245 A1 | 8/2006 | Schiller et al. | |
| 2007/0089740 A1 * | 4/2007 | Baumert | A61M 16/0488 128/200.24 |
| 2012/0272956 A1 * | 11/2012 | Rusher | A61M 16/209 128/205.24 |
| 2015/0202544 A1 | 7/2015 | Snee, Jr. et al. | |
| 2016/0375213 A1 | 12/2016 | Zlupko | |
| 2017/0333661 A1 * | 11/2017 | Bennett | A61M 16/0866 |
| 2019/0290959 A1 * | 9/2019 | Chesbrough | A61M 21/02 |
| 2020/0086074 A1 * | 3/2020 | Rusher | A61M 16/0866 |

OTHER PUBLICATIONS

Netherlands Patent Office, Search Report and Written Opinion from Netherlands Application No. N2019578 pp. 1-13, publisher Netherlands Patent Office, published Rijswijk, The Netherlands, dated Sep. 19, 2017; copy enclosed (13 pages).

European Patent Office, Communication Pursuant to Article 94(3) EPC, Communication regarding European Application No. 18822476.0-1122; pp. 1-8, publisher European Patent Office, published Rijswijk, The Netherlands, dated Feb. 10; copy enclosed (8 pages).

* cited by examiner

BREATH CONTROL DEVICE

CROSS-REFERENCE TO RELATED APPLICATIONS

The present application is a national entry under 35 U.S.C. 371 of International Application No. PCT/IB2018/001146 having international filing date Sep. 12, 2018, which claims priority to Dutch Application Serial No. 2019578 filed Sep. 19, 2017, which issued as Dutch Patent No. 2019578 on Mar. 28, 2019, the contents of which are hereby incorporated by reference in its entirety.

FIELD OF THE INVENTION

The invention relates to a breath control device comprising at least one longitudinal tube with a wall provided with at least a resilient part.

US 2015/0202544 relates to a device designed to assist persons who fidget, wherein fidgeting is defined to consist of actions that are conducted by persons as a means to release internal tension so as to allow the person to better concentrate, focus and complete tasks that would be problematic without the ability to fidget. One known way of fidgeting is manipulating a pen or a cigarette. Particularly pens that are embodied with a longitudinal tube with an at least in part resilient wall are desirable objects to fidget with, as are cigarettes that are resilient in themselves.

The invention is aimed at providing a much simpler and smaller tool for fidgeting then is known from US 2015/0202544 and healthier than cigarettes, so that the fidgeting tool of the invention will be easy for the person who wants to make use of it to carry along.

The invention is based on the insight that persons who fidget do that to release tension, which is at many times also a cause for people to experience breathing problems and to resort to breathing exercises.

Research has shown that in particular resistance breathing can reduce anxiety, depression, and generally improves human well-being. The invention is therefore aimed at providing a tool with dual functionality, however both aimed at reducing a person's tension.

The device of the invention is therefore embodied with the features of one or more of the appended claims.

In a first aspect of the invention the tube of the device is embodied with a proximal end and a distal end, and that the wall of the tube is provided with one or more at least in part and user-controlled closable openings or slits so that the fidgeting device also embodies a breath exercise device enabling resistance breathing. Preferably the proximal end is open and embodied as a mouthpiece and the distal end is closed.

An important aspect of this invention is that it enables active user-control of breathing resistance. The user can readily fluctuate the resistance of air passage, which introduces a 'fidgeting' feature for breathing exercises. Controlled resistance also enables breathing exercises to be optimized based upon personal preference and/or professional training.

The device of the invention can, through fidgeting, stimulate muscle motions in the hands and mouth, while simultaneously enabling customizable inlet and outlet air flow through the closable openings or slits for the breathing exercises. User controlled inlet/outlet air flow allows the user to customize breath resistance for optimal relaxation and/or selective exercises, such as yoga, alternative breathing techniques and clinical applications. Its simple construction makes the fidgeting device of the invention also an attractive respiratory device that regulates breath without harmful substances or disruptive odours. It is easy to carry and conceal on the body for use in recreational and professional environments. The device is further useful for people with limited respiratory capabilities including but not limited to chronic obstructive pulmonary disease (COPD) such as emphysema, asthma, and bronchitis, that can benefit from a respiratory exercise device.

In the simplest form of the device according to the invention the openings or slits are basically open to the atmosphere, and the amount of resistance during breathing is controlled by the user manipulating the degree of opening of said openings or slits by physical contact using the fingers or thumb.

In a more developed configuration of the device of the invention a piston is applied in the tube, wherein the piston is operable by a user by a trigger outside of the tube that directly or indirectly connects to the piston in the tube. The piston then closes off the tube at the distal side of the mouthpiece which is positioned at the proximal open end of the tube. The position of the piston may be selected by the user based on preference or on a specific respiratory exercise. It is preferred that the trigger connects to the piston with a stem that protrudes through one of the openings or slits, which is a simple form for controlling the position of the piston. Other options are that the piston is controlled by a small motor which is actuated by the user with a switch on the tube. This switch for the motor drive then acts as the trigger.

To support and realize different modes of fidgeting pleasure it may be preferable that the piston is spring-loaded by a spring or springs in the tube. Through the use of different spring stiffnesses and geometric configurations (e.g., linear, torsional, cam spring units), various tactile sensations can be generated to assist in fidget relaxation and/or personal preference in fidgeting.

It is preferable that when plural springs are applied, the springs are placed on opposite sides of the piston, for instance top and bottom, or left and right with respect to the piston. To be precise: such sides are preferably opposite of the piston in the longitudinal direction of the tube and/or adjacent to the piston between said piston and the wall of the tube.

The trigger of the piston does not need to be manipulated by the user but can also serve as a tool to measure the degree of inhalation and/or exhalation airflow and force rates for user performance feedback.

In order to support the breathing exercise function it may be preferable that the trigger is fixable in position by a rotary movement of the trigger circumferentially along the wall of the tube to position the stem in one of a series of grooves along the openings or slits in the wall of the tube.

In another embodiment the tube may be provided with pushbutton control. In that embodiment the device is preferably provided with spring-loaded closing plates for partly or completely closing off the openings in the wall of the tube, which closing plates are operable and connect with said pushbuttons to be able to manipulate a degree of opening that the closing plates provide to the openings in the wall of the tube.

In still another embodiment that promotes the breathing exercise function one or more slidable ball bearings are applied inside the tube.

It is expressly pointed out that the device of the invention comprises at least one longitudinal tube. This means that there may also be plural longitudinal tubes which are placed adjacent to each other, and which preferably have the ability to move relative to each other in a rotary movement to support fidgeting pleasure both in hand and in mouth.

The invention will hereinafter be further elucidated with reference to the drawing of an exemplary embodiment of a device according to the invention that is not limiting as to the appended claims.

In the drawing.

Whenever in the figures the same reference numerals are applied, these numerals refer to the same parts.

Figure 1A:
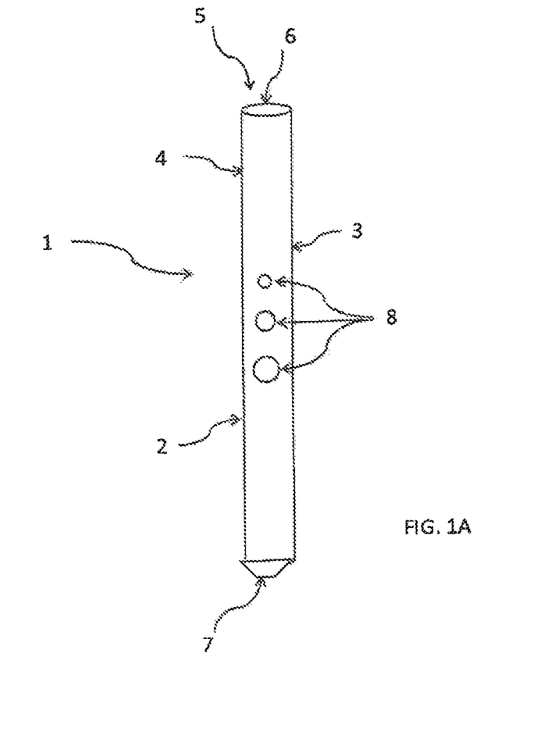
FIGS. 1A and 1B show different embodiments of a device according to the invention.
Figure 1B:
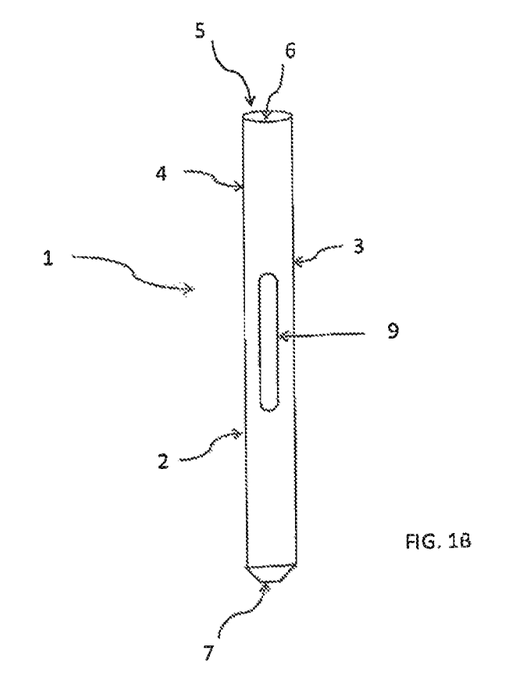

Both FIG. 1A and FIG. 1B show the most simple construction of the fidgeting device 1 of the invention comprising at least one longitudinal tube 2 with a wall 3 with at least a resilient part 4 which is preferably located at the mouthpiece 5, and wherein the tube 2 is embodied with a proximal open end 6 and a closed distal end 7, wherein the wall 3 of the tube 2 is provided with one or more closable openings 8 or slits 9 so that the fidgeting device 1 also embodies a breath exercise device. The openings 8 or slits 9 are at least in part or completely closable using someone's fingers or thumb.

Figure 2A:
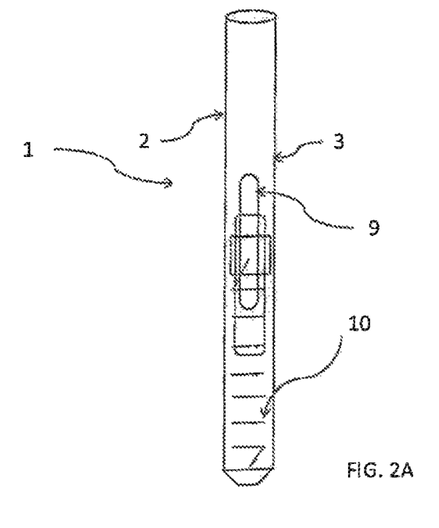
FIGS. 2A-D show another embodiment of a device according to the invention and its parts.
Figure 2B:
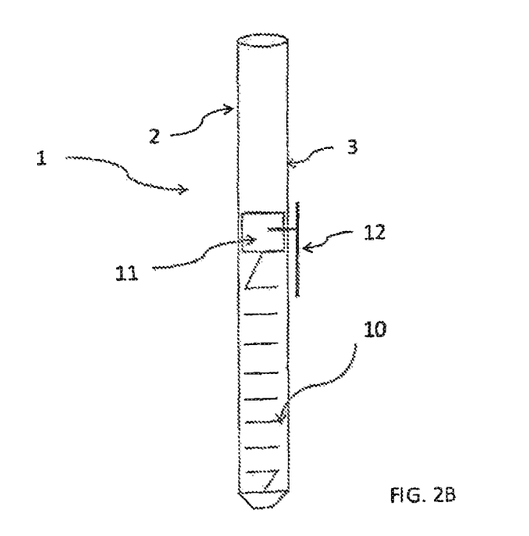
Figure 2C:
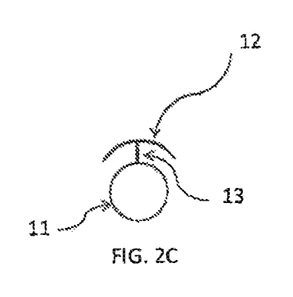
Figure 2D:
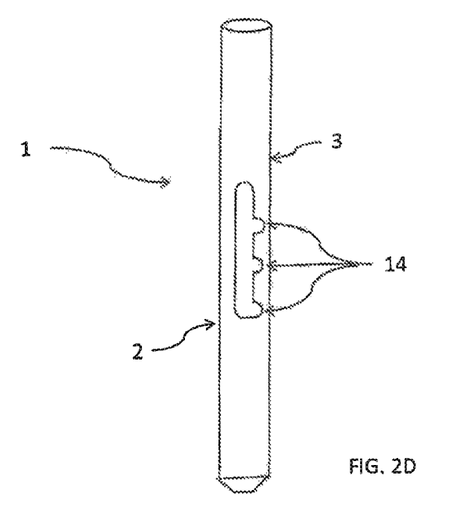

A more developed device 1 is shown in FIGS. 2A-2D. FIG. 2A shows a tube 2 with a partly translucent wall 3 showing that inside the tube 2 a spring 10 is applied. In the cross-sectional side view of FIG. 2B it is shown that the spring 10 acts on a piston 11 to give the piston a preferential position within the tube 2. On the piston 11 a trigger 12 is mounted with a stem 13 that reaches through the slit 9 in the tube 2 and enables the user to manipulate the position of the piston 11 within the tube 2 by sliding the trigger 12 so as to influence the amount of resistance during the user's breathing exercises. A frontal view of the piston 11 with the trigger 12 mounted thereon with the stem 13 is shown in FIG. 2C. In FIG. 2D it is shown that the trigger is fixable in position by a rotary movement of the trigger 12 circumferentially along the wall 3 of the tube 2 so as to arrange that the stem 13 which connects the trigger 12 to the piston 11 can be locked into one of a series of grooves 14 next to the slit 9 in the tube 2.

Figure 3:
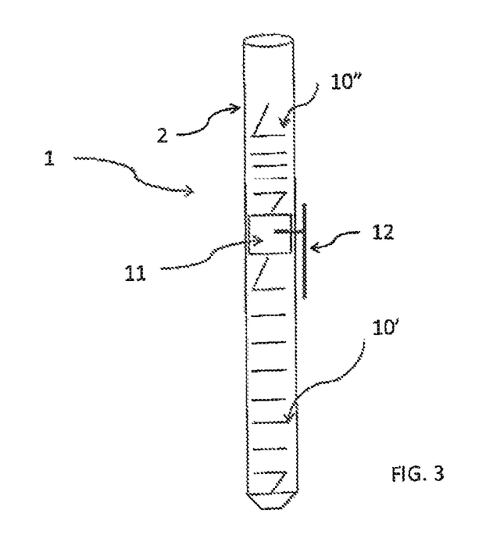
FIG. 3 shows still another embodiment of a device according to the invention.

In FIG. 3 still another embodiment is shown wherein a cross-sectional side view of the tube 2 shows that the piston may be loaded with springs 10', 10" on opposite sides of the piston 11 in the longitudinal direction of the tube 2. Although not shown in the figures it is also possible that springs are provided adjacent to the piston 11 between said piston 11 and the wall 3 of the tube 2 in a manner as is done with the keys of a computer keyboard to provide a clicking experience. It will be clear for the skilled person that any one of the other features shown in FIGS. 2A-2D may also be applied in combination with the features of the embodiment of FIG. 3.

Regarding the position of the piston 11, an embodiment is possible wherein the stem 13 itself without a trigger mounted on it can serve as a visual indicator for the amount of inhalation and/or exhalation by the user and the breathing force applied with it. If still a trigger 12 is mounted on the stem 13, the trigger itself can also serve this purpose. For each case it is preferably that there are visual indicators along the wall 3 of the tube 2 to indicate the position of the stem 13 or the trigger 12.

Figure 5A:
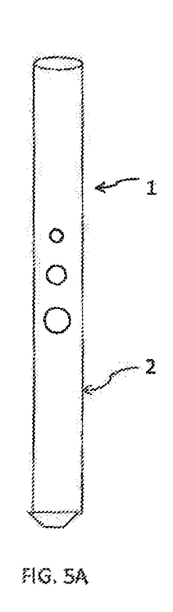
FIGS. 5A-5E shown embodiments of a device according to the invention with pushbutton's.
Figure 5B:
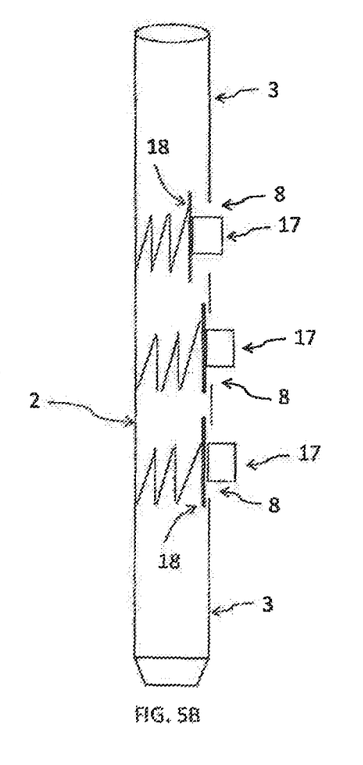

Instead of using a trigger which is mounted with a stem on a piston as depicted in FIGS. 2A-2D, FIGS. 5A-5E show an embodiment wherein the tube 2 is embodied with pushbuttons 17 that connect to closing plates 18 which partly or completely can close off openings 8 in the wall 3 of the tube 2, as is best shown in FIG. 5B. The closing plates 18 are spring-loaded with a spring 19 that urges the closing plates 18 into a closed position against the interior of the wall 3 of the tube 2. In that situation hardly any air can pass the closed off openings 8.

Figure 5D:
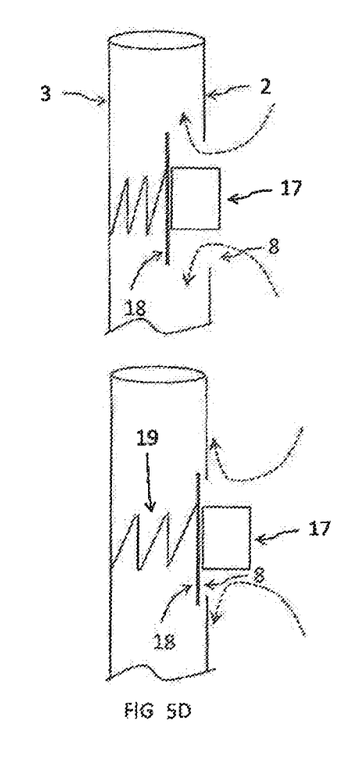
Figure 5F:
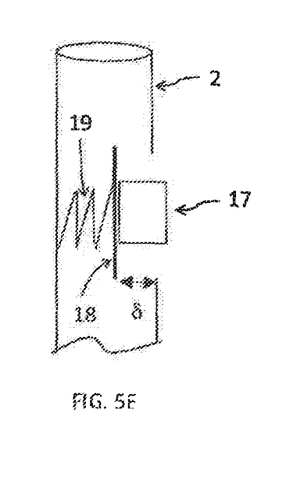

FIG. 5C depicts a situation relating for clarity to only one of the pushbuttons. It shows that a pushbutton 17 is pushed down to a certain extent into the tube 2, so as to release the spring-loaded closing plate 18 from the interior of the wall 3 of the tube 2, which opens the opening 8 for the passage of air. Conversely FIG. 5D shows the situation wherein said pushbutton 17 is released and wherein the closing plate 18, because of it being spring-loaded by the spring 19, is urged back against the interior of the wall 3 of the tube 2 to close off the concerning opening 8.

FIG. 5E symbolizes that the level of depressing 'Delta' of the pushbutton 17 is user controlled, which influences the amount of possible air passage through the opening 8 and thus adds a fidgeting feature for breathing exercises.

Figure 4A:
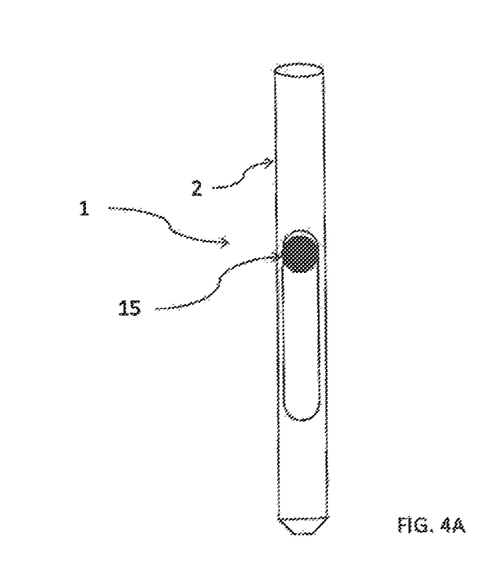
FIGS. 4A and 4B shows yet another embodiment of a device according to the invention.
Figure 4B:
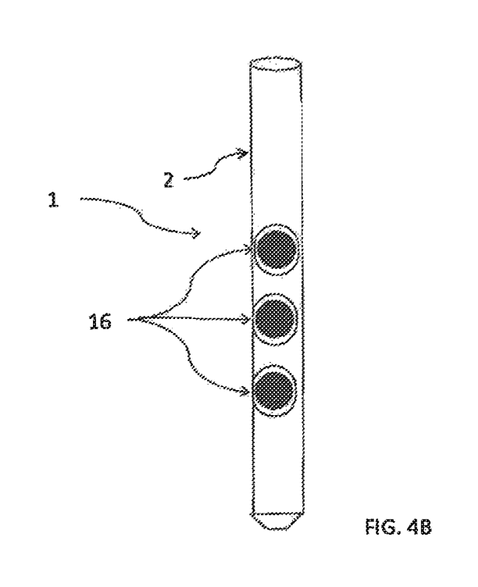

Finally FIGS. 4A and 4B show an embodiment in which a ball bearing slider mechanism 15 is applied (FIG. 4A), or in which a roller mechanism 16 is applied in which multiple independent bearings are rotationally positioned in the tube 2 (FIG. 4B).

Although the invention has been discussed in the foregoing with reference to an exemplary embodiment of the device of the invention, the invention is not restricted to these particular embodiments which can be varied in many ways without departing from the invention. The discussed exemplary embodiments shall therefore not be used to construe the appended claims strictly in accordance therewith. On the contrary the embodiments are merely intended to explain the wording of the appended claims without intent to limit the claims to these exemplary embodiments. The scope of protection of the invention shall therefore be construed in accordance with the appended claims only, wherein a possible ambiguity in the wording of the claims shall be resolved using these exemplary embodiments.

It is for instance possible that additional tubes can be attached for customizable features including but not limited to aesthetic features, tactile sensation components, and/or diagnostic respiratory sensors. For example, mechanical or mechatronics subassemblies encased within the at least one of the tubes can provide features such as tactile sensations and/or visual displays and/or textile sensations.

The invention claimed is:

1. A breath control device comprising:
   at least one longitudinal tube having a wall provided with at least one resilient part, an open proximal end configured to permit a flow of air therethrough, and a closed distal end;
   at least one opening formed in said wall and configured to permit said flow of air therethrough,
   a spring within said tube;
   a piston biased against said spring and slidably movable within said tube; and
   a stem affixed to said piston and extending through said at least one opening;

wherein said piston is selectively movable within said tube to selectively adjust an amount of air resistance provided by said piston by one of: (i) selective movement of the stem, and (ii) flow of air in said tube against said piston.

2. The breath control device according to claim 1, further comprising a trigger connected to said piston inside said tube, said trigger extending outside said tube, said piston being operable by manipulating said trigger outside said tube.

3. The breath control device according to claim 2, wherein said trigger connects to said piston by said stem.

4. The breath control device according to claim 2, further comprising at least one groove along said at least one opening, and wherein said trigger is fixable in position by a rotary movement of said trigger circumferentially along said wall of said tube to position said stem in one of said at least one groove along said at least one opening.

* * * * *